United States Patent
Kamal et al.

(10) Patent No.: US 7,015,215 B2
(45) Date of Patent: Mar. 21, 2006

(54) PYRROLO[2,1-C][1,4] BENZODIAZEPINES COMPOUNDS AND PROCESS THEREOF

(75) Inventors: Ahmed Kamal, Hyderabad (IN); Peram Surakattula Murali Mohan Reddy, Hyderabad (IN); Depatla Rajasekhar Reddy, Hyderabad (IN)

(73) Assignee: Council of Scientific and Industrial Research, New Dehli (IN)

( * ) Notice: Subject to any disclaimer, the term of this patent is extended or adjusted under 35 U.S.C. 154(b) by 344 days.

(21) Appl. No.: 10/401,754

(22) Filed: Mar. 31, 2003

(65) Prior Publication Data

US 2004/0192678 A1    Sep. 30, 2004

(51) Int. Cl.
   C07D 519/00    (2006.01)
   A61K 31/5517   (2006.01)
   A61P 35/00     (2006.01)

(52) U.S. Cl. ........................ 514/220; 540/496
(58) Field of Classification Search ........ 540/496; 514/220
   See application file for complete search history.

(56) References Cited

OTHER PUBLICATIONS

S. Kunimoto et al., The Journal of Antibiotics, 1980, vol. XXXIII, No. 6, pp. 665-667.

D. Kaplan et al., Biochemistry, 1981, vol. 20, pp. 7572-7580.

D. Thurston et al., J. Org. Chem., 1996, vol. 61, pp. 8141-8147.

*Primary Examiner*—Bruck Kifle
(74) *Attorney, Agent, or Firm*—Birch, Stewart, Kolasch & Birch

(57) ABSTRACT

The present invention provides Analogues of 1,1'-{[(bisalkane-1,N-diyl)piperazine]dioxy}bis(11aS)-7-methoxy-1,2,3,11a-tetrahydro-5H-pyrrolo[2,1-c][1,4]benzodiazepin-5-one] of formula (VI)

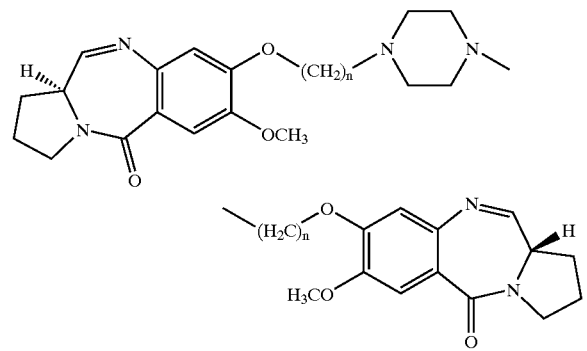

Figure 1:
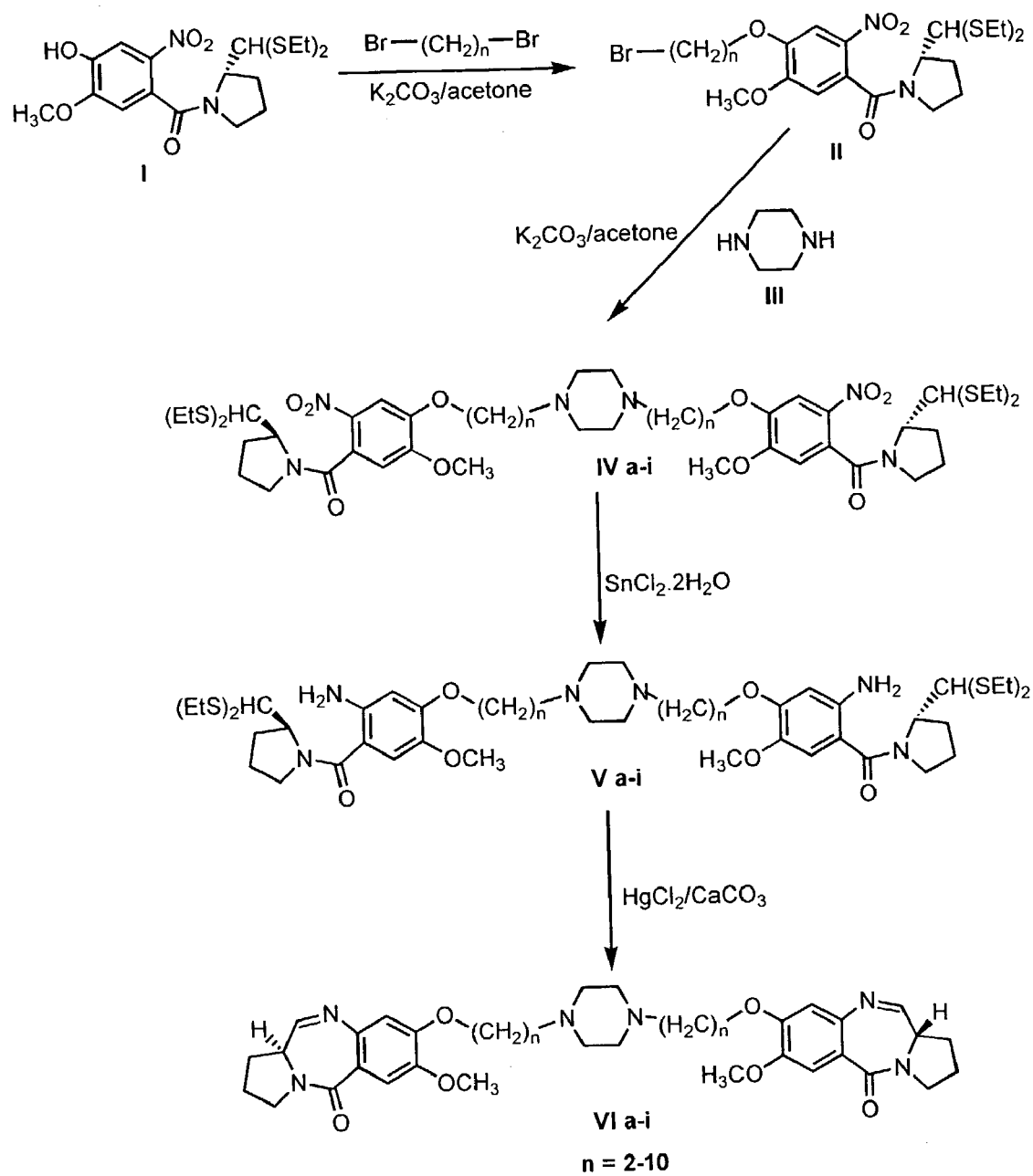

where n=2 to 10; a pharmaceutical composition comprising the above analogs and a process of preparing these analogues.

9 Claims, 1 Drawing Sheet n = 2-10

PYRROLO[2,1-C][1,4] BENZODIAZEPINES COMPOUNDS AND PROCESS THEREOF

FIELD OF THE INVENTION

The present invention relates to novel pyrrolo[2,1-c][1,4] benzodiazepines useful as potential antitumour agents. This invention relates to a process for the preparation of new pyrrolo[2,1-c][1,4]benzodiazepines useful as antitumour agents. More particularly, it provides a process for the preparation of 1,1'-{[(bisalkane-1,N-diyl)piperazine] dioxy}bis[(11aS)-7-methoxy-1,2,3,11a-tetrahydro-5H-pyrrolo[2,1-c][1,4]benzodiazepin-5-one, with aliphatic chain length variations for the compounds and it also describes the anticancer (antitumour) activity. The structural formula of novel pyrrolo[2,1-c][1,4]benzodiazepine is as follows, wherein n=2 to 10.

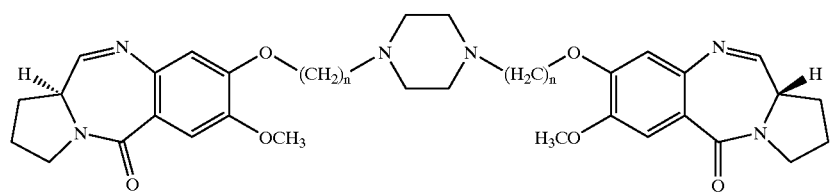

BACKGROUND AND PRIOR ART REFERENCES

Pyrrolo[2,1-c][1,4]benzodiazepines antitumour antibiotics are commonly known as anthramycin class of compounds. In the last few years, a growing interest has been shown in the development of new pyrrolo[2,1-c][1,4]benzodiazepines (PBDs). These antibiotics react covalently with DNA to form an N2-guanine adduct that lies within the minor groove of duplex DNA via an acid-labile aminal bond to the electrophilic imine at the N10-C11 position. (Kunimoto, S. Masuda, T. Kanbayashi, N. Hamada, M. Naganawa, H. Miyamoto, M. Takeuchi, T. and Unezawa, H. *J. Antibiot.*, 1980, 33, 665.; Kohn, K. W. and Speous, C. L. *J. Mol. Biol.*, 1970, 51, 551.; Hurley, L. H. Gairpla, C. and Zmijewski, M. *Biochem. Biophys.* Acta., 1977, 475, 521.; Kaplan, D. J. and Hurley, L. H. *Biochmestry*, 1981, 20, 7572). The molecules have a right-handed twist, which allows them to follow the curvature of the minor groove of B-form double-stranded DNA spanning three base pairs. Recently PBD dimers have been developed that comprises two C2-exo-methylene-substituted DC-81 subunits tethered through their C-8 position via an inert propanedioxy linker. (S. J. Gregson, P. W. Howard, J. A. Hartely, N. A. Brooks, L. J Adams, T. C. Jenkins, L. R. Kelland, and D. E. Thurston. *J. Med. Chem.*, 2001, 44, 737). A recent development has been the linking of two PBD units through their C-8 positions to give bisfunctional alkylating agents capable of cross-linking DNA (Thurston, D. E. Bose, D. S. Thomson, A. S. Howard, P. W. Leoni, A. Croker, S. J. Jenkins, T. C. Neidle, S. and Hurley, L. H. *J. Org. Chem.*, 1996, 61, 8141–8147). Recently, a noncross-linking mixed imine-amide PBD dimers have been synthesized that have significant DNA binding ability and potent anti tumour activitiy (Kamal, A.; Laxman, N.; Ramesh, G.; Ramulu, P and Srinivas, O. U.S. Pat. No. 636,233. dt 26-03-2002.; Kamal, A.; Ramesh, G.; Laxman, N.; Ramulu, P.; Srinivas, O.; Neelima, K.; Kondapi, A. K.; Srinu, V. B.; Nagarajaram, H. M. *J. Med Chem.* 2002, 45, 4679).

Naturally occurring pyrrolo[2,1-c][1,4]benzodiazepines belong to a group of antitumour antibiotics derived from *Streptomyces* species. Recently, there is much

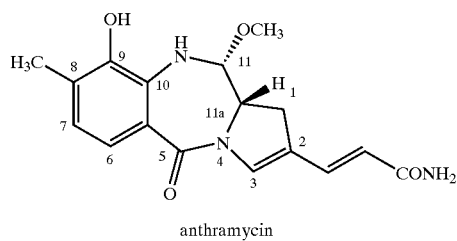

anthramycin

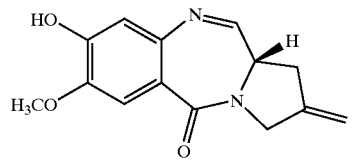

C2-exo-methylene-substituted DC-81

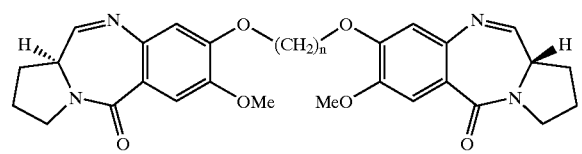

DC-81 dimers (n = 3–5); DSB-120 (n = 3)

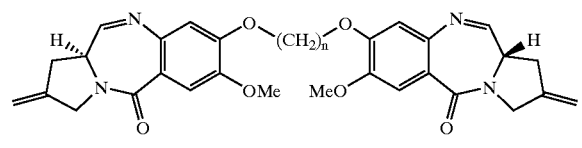

SJG-136 impetus for the PBD systems as they can recognize and bind to specific sequence of DNA. Examples of naturally occurring PBD's include anthramycin, DC-81, tomaymycin, sibiromycin and neothramycin.

However, the clinical efficacy for these antibiotics is hindered by several limitations, such as poor water solubility and cardiotoxicity and development of drug resistance and metabolic inactivation.

OBJECTS OF THE INVENTION

The main object of the present invention is to provide new pyrrolo[2,1-c][1,4]benzodiazepines useful as antitumour agents.

Another object of the invention is to provide pharmaceutical compositions comprising novel pyrrolo[2,1-c][1,4]benzodiazepines useful as anti-cancer agents Another objective of the present invention is to provide a process for the preparation of novel pyrrolo[2,1-c][1,4] benzodiazepines.

SUMMARY OF THE INVENTION

Accordingly, the present invention provides novel pyrrolo [2,1-c][1,4]benzodiazepine of formula VI where n is 2 to 10; and a process for the preparation of the same.

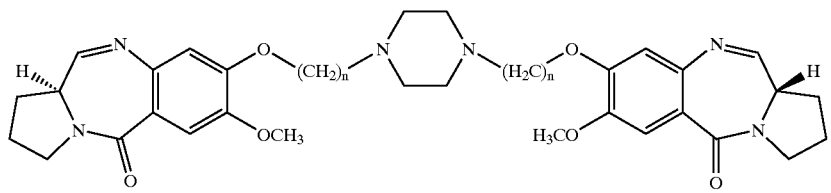

DETAILED DESCRIPTION OF THE INVENTION

In accordance, the present invention provides analogues of 1,1'-{[(bisalkane-1,N-diyl)piperazine]dioxy}bis(11aS)-7-methoxy-1,2,3,11a-tetrahydro-5H-pyrrolo[2,1-c][1,4]benzodiazepin-5-one] of formula (VI)

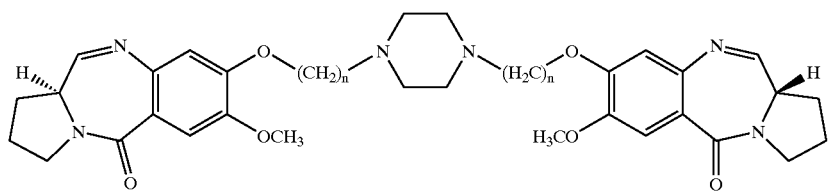

where n=2 to 10

Another embodiment of the invention provides a novel pyrrolobenzodiazepine having structural formula as shown below. (n=2)

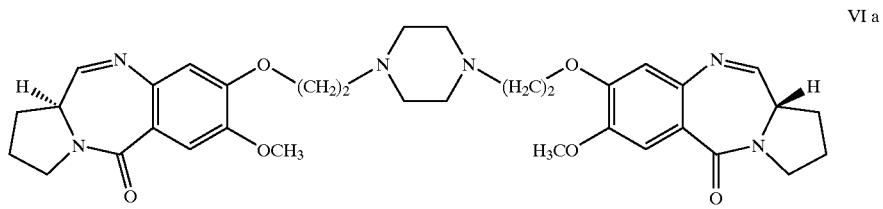

VI a

Still another embodiment, the invention provides novel pyrrolobenzodiazepine having structural formula as shown below. (n=3)

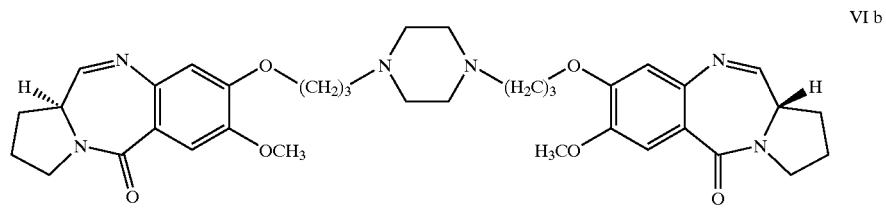

VI b

Still another embodiment, the invention provides novel pyrrolobenzodiazepine having structural formula as shown below. (n=4)

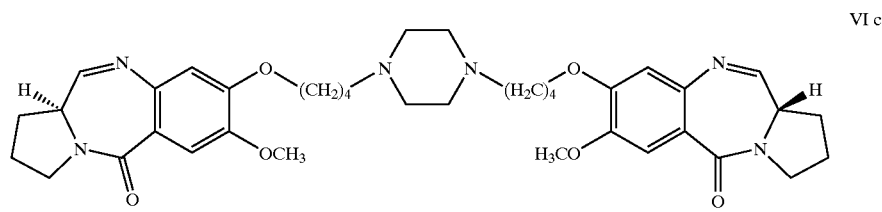

VI c

Still another embodiment, the invention provides novel pyrrolobenzodiazepine having structural formula as shown below. (n=5)

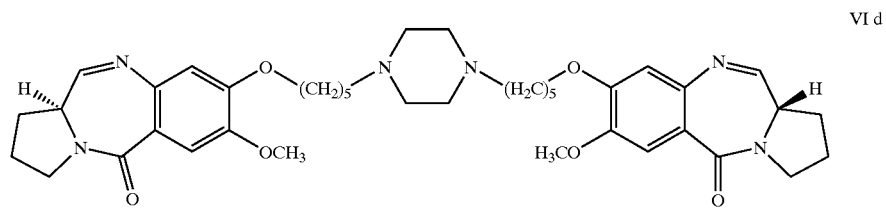

VI d

Still another embodiment, the invention provides novel pyrrolobenzodiazepine having a structural formula as shown below. (n=6)

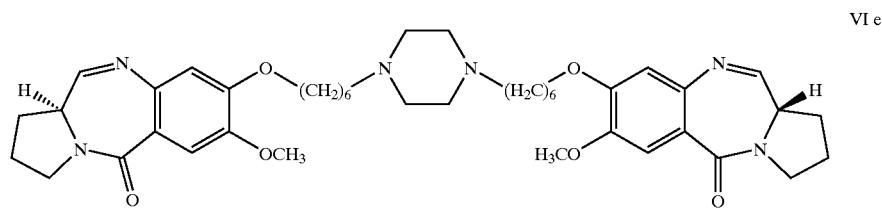

VI e

Still yet another embodiment, the invention provides novel pyrrolobenzodiazepine having structural formula as shown below. (n=7)

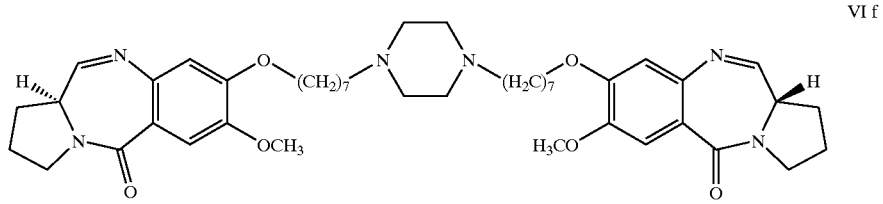

VI f

Yet another embodiment, the invention provides novel pyrrolobenzodiazepine having structural formula as shown below. (n=8)

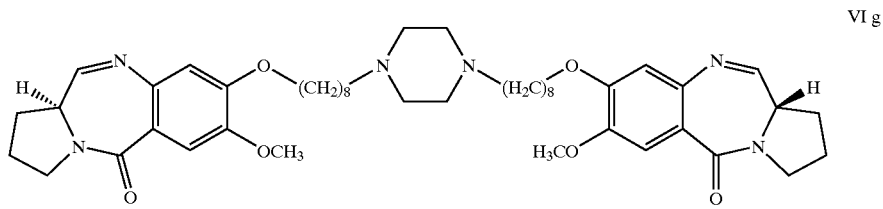

VI g

Still yet another embodiment, the invention provides novel pyrrolobenzodiazepine having structural formula as shown below. (n=9)

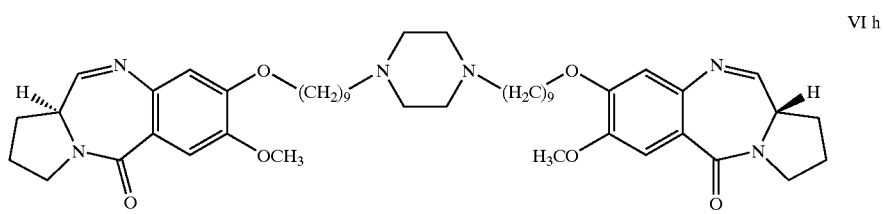

VI h

Still yet another embodiment, the invention provides novel pyrrolobenzodiazepine having structural formula as shown below. (n=10)

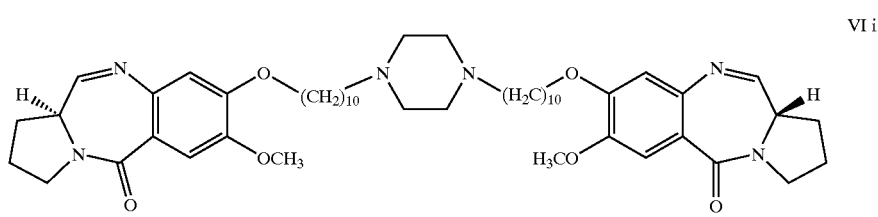

VI i

In an embodiment of the inventioin provides a process for the preparation of analogues of 1,1'-{[(bisalkane-1,N-diyl) piperazine]dioxy}bis(11aS)-7-methoxy-1,2,3,11a-tetrahydro-5H-pyrrolo[2,1-c][1,4]benzodiazepin-5-one] of formula (VI), the said process comprising steps of:

a) reacting compound of formula (I) with 1,2-dibromoethane in water miscible organic solvent in presence of a base at a reflux temperature for a period of 20 h to 48 h, b) pouring the reaction mixture of step (a) onto water, extracting with ethylacetate separating ethylacetate layer and discarding aqueous layer, c) evaporating the ethylacetate layer of step (b) to obtain a residue which is further purified to obtain pure compound of formula (II), d) providing a solution of formula (II) in a ketonic solvent in presence of a base at a reflux temperature for a period of 20 h to 48 h, e) pouring the reaction mixture of step (d) onto water, extracting with ethylacetate, separating ethylacetate layer, evaporating ethylacetate layer to obtain a residue, purifying the residue to get compound of formula (IV), f) dissolving compound of formula (IV) in alcohol, adding stannous chloride dihydrate, refluxing for 0.5 h to 1.5h, g) adjusting the pH of the reaction mixture of step (f) to 8.0 using alkali bicarbonate solution, h) extracting solution of pH 8.0 of step (g) with ethylacetate, separating ethylacetate extract, drying ethylacetate extract over anhydrous sodium sulphate, filtered and evaporated ethyl acetate solution to yield a crude compound of formula (V), i) dissolving compound of formula (V) of step (h) in a mixture of acetonitrile/water, adding mercuric chloride, mercuric oxide and stirred for 6 h to 12 h at an ambient temperature, j) evaporating organic layer of step (i), diluting the residue with ethylacetate, adding saturated bicarbonate solution at room temperature, filtering through celite bed, washed with ethyl acetate to obtain a clear filterate; and k) evaporating filtrate of step (j) to obtain a residue which is purified over silica gel column to yield pure compound of formula (VI).

Another embodiment of the invention, the base used is selected from a group consisting of lithium carbonate, sodium carbonate, potassium carbonate or cesium carbonate.

Another embodiment of the invention the ketonic solvent used is selected from a group consisting of acetone, methyl ethyl ketone and methyl isobutylketone.

Another embodiment of the invention the alcohol used is selected from methanol, ethanol and isopropanol, preferably methanol.

One more embodiment of the invention provides a pharmaceutical composition useful as anti-tumor agent, said composition comprising an effective amount of one or more analogues of 1,1'-{[(bisalkane-1,N-diyl)piperazine]dioxy}bis(11aS)-7-methoxy-1,2,3,11a-tetrahydro-5H-pyrrolo[2,1-c][1,4]benzodiazepin-5-one] of formula (VI).

Still another embodiment the composition optionally comprising of pharmaceutically acceptable additives.

Yet another embodiment, the composition is administered to mammals including human beings.

Yet another embodiment, the composition may be administered orally, systemically or by any other conventional methods The process for preparation of pyrrolo[2,1-c][1,4]benzodiazepines of formula VI of the drawing accompanying the specification wherein n is 2 to 10 which comprises: reacting (2S)-N-[4-hydroxy-5-methoxy-2-nitrobenzoyl]-2-carboxaldehyde diethylthioacetal of formula I with dibromoalkanes in an aprotic water miscible organic solvents like acetone, THF, and DMF in presence of a mild inorganic bases like $K_2CO_3$, $CsCO_3$ and $BaCO_3$ upto refluxing temperature for a period up to 48 hours, isolating (2S)-N-[4-(n-bromoalkoxy)-5-methoxy-2-nitrobenzoyl]pyrrolidine-2-carboxaldehyde diethyl thioacetal of formula II with piperazine of formula III in presence of mild inorganic bases like $K_2CO_3$, $CsCO_3$, and $BaCO_3$ and in presence of aprotic water miscible organic solvents upto refluxing for a period 48 hours isolating 1,1'-{[(bis alkane-1,N-diyl)piperazine]dioxy}bis[(11aS)-7-methoxy-2-nitrobenzoylpyrrolidin-2-carbox-aldehyde diethylthioacetal] IV where n is 2–10 by conventional methods, reducing the above nitro compounds of formula IV with $SnCl_2.2H_2O$ in presence of organic solvent up to a reflux temperature, isolating the 1,1'-{[(bisalkane-1,N-diyl)piperazine]dioxy}bis[(11aS)-7-methoxy-2-aminobenzoylpyrrolidin-2-carboxaldehyde diethyl thioacetal] of formula V where n is 2–10 by known methods, reacting the above said amino compound of formula V with known deprotecting agents in a conventional manner to give novel pyrrolo[2,1-c][1,4]benzodiazepines of formula VI wherein n are as stated above.

The precursor, (2S)-N-(4-hydroxy-2-methoxy-2-nitrobenzoyl)pyrrolidine-2-carboxaldehyde diethyl thioacetal of formula I (intermediates of DC-81) prepared by literature methods (Thurston, D. E.; Murthy, V. S.; Langley, D. R.; Jones, G. B. *Synthesis*, 1990, 81)

Some representative compounds of formula VI present invention are given below 1) 1,1'-{[(bisethane-1,N-diyl)piperazine]dioxy}bis[(11aS)-7-methoxy-1,2,3,11a-tetrahydro-5H-pyrrolo[2,1-c][1,4]benzodiazepin-5-one].

2) 1,1'-{[(bispropane-1,N-diyl)piperazine]dioxy}bis[(11aS)-7-methoxy-1,2,3,11a-tetrahydro-5H-pyrrolo[2,1-c][1,4]benzodiazepin-5-one].

3) 1,1'-{[(bisbutane-1,N-diyl)piperazine]dioxy}bis[(11aS)-7-methoxy-1,2,3,11a-tetrahydro-5H-pyrrolo[2,1-c][1,4]benzodiazepin-5-one].

These new analogues of pyrrolo[2,1-c][1,4]benzodiazepinedimers linked at C-8 position through piperazine moiety have shown promising anticancer activity in various cell lines. The molecules synthesized are of immense biological significance with potential sequence selective DNA-binding property. This resulted in design and synthesis of new congeners as illustrated in Scheme-1, which comprise:

1. The ether linkage at C-8 position of DC-81 intermediates with piperazine moiety
2. Refluxing the reaction mixture for 24–48 h.
3. Synthesis of C-8 linked PBD antitumour antibiotic dimer imines.
4. Purification by column chromatography using different solvents like ethylacetate, hexane, dichloromethane and methanol.

The process of preparation of new non-cross linking pyrrolo[2,1-c][1,4]benzodiazepines is disclosed and claimed in applicant's co-pending application Ser. No. 10/401,782.

The following examples are given by way of illustration and therefore should not be construed to the present limit of the scope of invention.

BRIEF DESCRIPTION OF ACCOMPANYING DRAWING

FIG. 1 represents schematic diagram of preparing compound of general formula VI (a–i).

EXAMPLE 1

A solution of (2S)-N-(4-hydroxy-5-methoxy-2-nitrobenzoyl)pyrrolidine-2-carbox-aldehyde diethylthioacetal of formula I (800 mg, 2 mmol), 1,2-dibromoethane (940 mg, 2.5 mmol) and $K_2CO_3$ (828 mg, 3 mmol) in dry acetone (40 ml) was refluxed for 48 h. After the completion of reaction as indicated by TLC, EtOAc-hexane (7:3), the reaction mixture was poured on to the water and then extracted with ethylacetate. Evaporation of the organic layer gave the crude product, which was further purified by column chromatography on silica gel eluting with EtOAc-hexane (1:1) gave the pure (2S)-N-[4-(2-bromoethoxy)-5-methoxy-2-nitrobenzoyl]pyrrolidine-2-carboxaldehyde diethyl thioacetal of formula II.

¹H NMR:(CDCl₃) Γ 1.20–1.4 (m, 6H), 1.75–2.2 (m, 4H), 2.6–2.9 (m, 4H), 3.20–3.33 (m, 2H), 3.67 (t, 2H), 3.95 (s, 3H); 4.37 (t, 2H), 4.62–4.78 (m, 1H), 4.85 (d, 1H), 6.82 (s, 1H), 7.67 (s, 1H).

A solution of (2S)-N-[4-(3-bromoethoxy)-5-methoxy-2-nitrobenzoyl]pyrrolidine-2-carboxaldehyde diethylthioacetal of formula II (507 mg, 1 mmol), piperazine(0.043 mg, 0.5 mmol) of the formula III and K₂CO₃ (414 mg, 3 mmol) in dry acetone (20 ml) was refluxed for 48 h. After the completion of reaction as indicated by TLC, EtOAc, the reaction mixture was poured on to the water and then extracted with ethylacetate. Evaporation of the organic layer gave the crude product, which was further purified by column chromatography on silica gel eluting with EtOAc-hexane (9:1) gave the pure 1,1'-{[(bisethane-1,N-diyl)piperazine]dioxy}bis[(11aS)-7-methoxy2-nitro-benzoylpyrrolidin-2-carboxaldehyde diethylthioacetal].

¹H NMR (CDCl₃) Γ 1.29–1.41 (m, 12H), 1.7–2.39 (m, 8H), 2.60–2.90 (m, 20H), 3.17–3.3 (m, 4H),3.92 (s, 6H), 4.2 (t, 4H), 4.60–4.70 (m, 2H), 4.81 (d, 2H), 6.8 (s, 2H), 7.7 (s, 2H).

FAB MS 939(M+H)⁺·

The 1,1'-{[(bisethane-1,N-diyl)piperazine]dioxy}bis[(11aS)-7-methoxy-2-nitro-benzoylpyrrolidin-2-carboxaldehyde diethylthioacetal] IV (939 mg, 1.0 mmol) was dissolved in methanol (10 mL) and added SnCl₂.2H₂O (1.124 g, 5.0 mmol) was refluxed for 1.5 h. The reaction mixture was then carefully adjusted to pH 8 with saturated NaHCO₃ solution and then extracted with ethyl acetate (3×20 mL). The combined organic phase was dried over Na₂SO₄ and evaporated under vacuum to afford the crude The 1,1'-{[(bisethane-1,N-diyl)piperazine]dioxy}bis[(11aS)-7-methoxy2-aminobenzoylpyrrolidin-2-carboxaldehyde diethylthioacetal].

A solution of the 1,1'-{[(bisethane-1,N-diyl)piperazine]dioxy}bis[(11aS)-7-methoxy-2-aminobenzoylpyrrolidin-2-carboxaldehyde diethylthioacetal] of formula V (879 mg, 1 mmol), HgCl₂ (794 mg, 2.93 mmol) and HgO (686 mg, 3.18 mmol) in CH₃CN/H₂O (3:1, 15 ml) was stirred at room temperature for 12 h until TLC (EtOAc), indicates complete loss of starting material. Then organic layer is evaporated in vacuum and the residue is diluted with EtOAc. To this saturated NaHCO₃ was added slowly at room temperature and the mixture is filtered through celite and washed with ethylacetate. The filterate is evaporated in vacuum to get crude 1,1'-{[(bisethane-1,N-diyl)piperazine]dioxy}bis[(11aS)-7-methoxy-1,2,3,11a-tetrahydro-5H-pyrrolo[2,1-c][1,4]benzodiazepin-5-one] of formula VIa, which was further purified by column chromatography on silica gel eluting first with ethylacetate to remove traces of mercuric salts and further eluted with CHCl₃-methanol (9:1).

¹HNMR (CDCl₃) Γ 1.92–2.42 (m, 8H), 2.60–2.95 (m, 12H), 3.2–3.88 (m, 6H), 3.92(s, 6H), 4.14–4.28 (m, 4H), 6.76 (s, 2H), 7.5 (s, 2H), 7.66 (d, 2H).

FAB MS: 631 (M+H)⁺·

EXAMPLE 2

A solution of (2S)-N-(4-hydroxy-5-methoxy-2-nitrobenzoyl)pyrrolidine-2-carboxaldehyde diethylthioacetal of formula I (400 mg, 1 mmol), 1,3-dibromopropane (502 mg, 2.5 mmol) and K₂CO₃ (414 mg, 3 mmol) in dry acetone (20 ml) was refluxed for 48 h. After the completion of reaction as indicated by TLC, EtOAc-hexane (7:3), the reaction mixture was poured on to the water and then extracted with ethylacetate. Evaporation of the organic layer gave the crude product, which was further purified by column chromatography on silica gel eluting with EtOAc-hexane (1:1) gave the pure (2S)-N-[4-(4-bromopropoxy)-5-methoxy-2-nitrobenzoyl]pyrrolidine-2-carboxaldehyde diethylthioacetal of formula II.

¹H NMR: (CDCl₃) Γ 1.25–1.4 (m, 6H), 1.85–2.35 (m, 4H), 2.38–2.5 (m, 2H), 2.6–2.9 (m, 4H), 3.18–3.33 (m, 2H), 3.64 (t, 2H), 3.97 (s, 3H); 4.29 (t, 2H), 4.67–4.78 (m, 1H), 4.83 (d, 1H), 6.78 (s, 1H), 7.7 (s, 1H).

A solution of (2S)-N-[4-(4-bromopropoxy)-5-methoxy-2-nitrobenzoyl]pyrrolidine-2-carboxaldehyde diethylthioacetal of formula II (520 mg, 1 mmol), piperazine (0.043 mg, 1 mmol) of the formula III and K₂CO₃ (414 mg, 3 mmol) in dry acetone (20 ml) was refluxed for 48 h. After the completion of reaction as indicated by TLC, EtOAc, the reaction mixture was poured on to the water and then extracted with ethylacetate. Evaporation of the organic layer gave the crude product, which was further purified by column chromatography on silica gel eluting with EtOAc-hexane (9:1) gave the pure of 1,1'-{[(bispropane-1,N-diyl)piperazine]dioxy}bis[(11aS)-7-methoxy-2-nitro benzoylpyrrolidin-2-carboxaldehyde diethylthioacetal].formula IV.

¹H NMR (CDCl₃) Γ 1.3–1.42 (m, 12H), 1.9–2.32 (m, 8H), 2.47–2.6 (m, 4H), 2.7–2.9 (m, 24H), 3.2–3.3 (m, 4H), 3.95 (s, 6H), 4.1–4.2 (t, 4H), 4.62–4.75 (m, 2H), 4.82 (d, 2H), 6.75 (s, 2H), 7.67 (s, 2H).

FAB MS: 967(M+H)⁺

The 1,1'-{[(bispropane-1,N-diyl)piperazine]dioxy}bis[(11aS)-7-methoxy-2-nitro benzoylpyrrolidin-2-carboxaldehyde diethylthioacetal] (966 mg, 1.0 mmol) of the formula IV was dissolved in methanol (10 ml) and added SnCl₂.2H₂O (1.124 g, 5.0 mmol) was refluxed for 1.5 h. The reaction mixture was then carefully adjusted to pH 8 with saturated NaHCO₃ solution and then extracted with ethyl acetate (3×20 ml). The combined organic phase was dried over Na₂SO₄ and evaporated under vacuum to afford the crude 1,1'-{[(bis propane-1,N-diyl)piperazine]dioxy}bis[(11aS)-7-methoxy 2-aminobenzoylpyrrolidin-2-carboxaldehyde diethylthioacetal]. of formula V. A solution of 1,1'-{[(bispropane-1,N-diyl)piperazine]dioxy}bis[(11aS)-7-methoxy 2-aminobenzoylpyrrolidin-2-carboxaldehyde diethylthioacetal] the formula V. (907 mg, 1 mmol), HgCl₂ (794 mg, 2.93 mmol) and HgO (687 mg, 3.18 mmol) in CH₃CN/H₂O (3:1, 15 ml) was stirred at room temperature for 12 h until TLC (EtOAc), indicates complete loss of starting material. Then organic layer is evaporated in vacuum and the residue is diluted with EtOAc. To this saturated NaHCO₃ was added slowly at room temperature and the mixture is filtered thorough celite and washed with ethylacetate. The filterate is evaporated in vacuum to get crude 1,1'-{[(bispropane-1,N-diyl)piperazine]dioxy}bis[(11aS)-7-methoxy-1,2,3,11a-tetrahydro-5H-pyrrolo[2,1-c][1,4]benzodiazepin-5-one] of formula VIb, which was further purified by column chromatography on silica gel eluting first with ethylacetate to remove traces of mercuric salts and further eluted with CHCl₃-methanol (9:1).

¹HNMR¹ (CDCl₃) Γ 1.92–2.37 (m, 8H), 2.57–2.8 (m, 16H), 3.32–3.75 (m, 6H), 3.95 (s, 6H) 4.12–4.45 (m, 4H), 6.85 (s, 2H), 7.52 (s, 2H), 7.82 (d, 2H)

FAB MS: 659 (M+H)⁺

EXAMPLE 3

A solution of (2S)-N-(4-hydroxy-5-methoxy-2-nitrobenzoyl)pyrrolidine-2-carboxaldehyde diethylthioacetal of formula I (400 mg, 1 mmol), 1,4-dibromobutane (540 mg, 2.5 mmol) and K₂CO₃ (414 mg, 3 mmol) in dry acetone (20 ml)

was refluxed for 48 h. After the completion of reaction as indicated by TLC, EtOAc-hexane (7:3), the reaction mixture was poured on to the water and then extracted with ethylacetate. Evaporation of the organic layer gave the crude product, which was further purified by column chromatography on silica gel eluting with EtOAc-hexane (1:1) gave the pure (2S)-N-[4-(5-bromobutanoxy)-5-methoxy-2-nitrobenzoyl]pyrrolidine-2-carboxaldehyde diethylthioacetal of formula II.

$^1$H NMR: (CDCl$_3$) Γ 1.3–1.45(m, 6H), 1.88–2.38 (m, 4H), 2.69–2.88 (m, 8H), 3.20–3.33 (m, 2H), 3.51 (t, 2H), 3.97 (s, 3H); 4.16 (t, 2H), 4.63–4.76 (m, 1H), 4.86(d, 1H), 6.79 (s, 1H), 7.67 (s, 1H).

A solution of (2S)-N-[4-(5-bromobutanoxy)-5-methoxy-2-nitrobenzoyl]pyrrolidine-2-carboxaldehyde diethylthioacetal of formula II. (53 mg, 1 mmol), piperazine(0.043 mg, 1 mmol) of formula III and K$_2$CO$_3$ (414 mg, 3 mmol) in dry acetone (20 ml) was refluxed for 48 h. After the completion of reaction as indicated by TLC, EtOAc, the reaction mixture was poured on to the water and then extracted with ethylacetate. Evaporation of the organic layer gave the crude product, which was further purified by column chromatography on silica gel eluting with EtOAc-hexane (9:1) gave the pure of 1,1'-{[(bisbutane-1,N-diyl)piperazine]dioxy}bis[(11aS)-7-methoxy-2-nitro benzoylpyrrolidin-2-carboxaldehyde diethylthioacetal] of formula IV.

$^1$H NMR (CDCl$_3$) Γ 1.30–1.43 (m, 12H), 2.74–2.35 (m, 12H), 2.51–2.66 (m, 16H), 3.20–3.3 (m, 4H), 3.97 (s, 6H), 4.12 (t, 4H), 4.64–4.76 (m, 2H), 4.87 (d, 2H), 6.84 (s, 2H), 7.66 (s, 2H).

FAB MS: 995 (M+H)$^+$

The of 1,1'-{[(bisbutane-1,N-diyl)piperazine]dioxy}bis[(11aS)-7-methoxy-2-nitro benzoylpyrrolidin-2-carboxaldehyde diethylthioacetal]. of formula IV (730 mg, 1.0 mmol) was dissolved in methanol (10 ml) and added SnCl$_2$.2H$_2$O (1.124 g, 5.0 mmol) was refluxed for 1.5 h. The reaction mixture was then carefully adjusted to pH 8 with saturated NaHCO$_3$ solution and then extracted with ethyl acetate (3×20 ml). The combined organic phase was dried over Na$_2$SO$_4$ and evaporated under vacuum to afford the crude of 1,1'-{[(bisbutane-1,N-diyl)piperazine]dioxy}bis[(11aS)-7-methoxy-2-aminobenzoylpyrrolidin-2-carboxaldehyde diethylthioacetal]. of formula V.

A solution of 1,1'-{[(bisbutane-1,N-diyl)piperazine]dioxy}bis[(11aS)-7-methoxy 2-aminobenzoylpyrrolidin-2-carboxaldehyde diethylthioacetal] formula V. (935 mg, 1 mmol), HgCl$_2$ (794 mg, 2.93 mmol) and HgO (687 mg, 3.18 mmol) in CH$_3$CN/H$_2$O (3:1, 15 ml) was stirred at room temperature for 12 h until TLC (EtOAc), indicates complete loss of starting material. Then organic layer is evaporated in vacuum and the residue is diluted with EtOAc. To this saturated NaHCO$_3$ was added slowly at room temperature and the mixture is filtered thorough celite and washed with ethylacetate. The filterate is evaporated in vacuum to get crude 1,1'-{[(bisbutane-1,N-diyl)piperazine]dioxy}bis[(11aS)-7-methoxy-1,2,3,11a-tetrahydro-5H-pyrrolo[2,1-c][1,4]benzodiazepin-5-one] VIc, which was further purified by column chromatography on silica gel eluting first with ethylacetate to remove traces of mercuric salts and further eluted with CHCl$_3$-methanol (9:1).

$^1$HNMR (CDCl$_3$) Γ 1.78–2.24 (m, 8H), 2.30–2.75 (m, 20H), 3.4–3.7 (m, 6H), 3.92 (s, 6H), 4.1–4.23 (m, 4H), 6.73 (s, 2H), 7.48 (s, 2H), 7.60 (d, 2H).

FAB MS 687 (M+H)$^+$

Biological Activity: In vitro biological activity studies were carried out at National Cancer Institute (U.S.A.).

Cytotoxicity: Compounds VIa–d were evaluated in vitro against sixty human tumour cells derived from nine cancer types (leukemia, non-small-cell lung, colon, CNS, melanoma, ovarian, prostate, and breast cancer). For each compound, dose response curves for each cell line were measured at a minimum of five concentrations at 10 fold dilutions. A protocol of 48 h continuous drug exposure was used, and a sulforhodamine B (SRB) protein assay was used to estimate cell viability or growth. The concentration causing 50% cell growth inhibition (GI50), total cell growth inhibition (TGI, 0% growth) and 50% cell death (LC50, −50% growth) compared with the control was calculated. The mean graph midpoint values of log$_{10}$TGI and log$_{10}$LC50 as well as log$_{10}$GI50 for VIa-d are listed in Table 1. As demonstrated by mean graph pattern, compound VIc exhibits an interesting profile of activity and selectivity for various cell lines. The mean graph mid point of log$_{10}$TGI and log$_{10}$LC50 showed similar pattern to the log$_{10}$GI50 mean graph mid points.

TABLE 1

Log$_{10}$ GI50 log$_{10}$ TGI and log$_{10}$ LC50 mean graphs midpoints (MG_MID) of in vitro Cytotoxicity data for the compounds VI a–d against human tumor cell lines.

| Compound | Log$_{10}$ GI50 | Log$_{10}$ TGI | Log$_{10}$ LC50 |
|---|---|---|---|
| VIa | −4.69 | −4.16 | −4.03 |
| VIb | −5.19 | −4.22 | −4.01 |
| VIc | −7.70 | −5.95 | −4.47 |
| VId | −5.14 | −4.26 | −4.04 |

The in vitro anticancer activity for four representative compounds has been given in Table 2. The comparison of the data of Table 2 reveals the importance of the alkane spacer. As the alkane spacer increased from 2–4 the cytotoxic activity has moderately enhanced. The 4-carbon spacer of compound VIc confers a suitable fit in the minor groove of double helix DNA and show slightly higher activity in this series of compounds VI a–d.

TABLE 2

Log LC50 (concentration in mol/L causing 50% lethality) Values for Compounds VI a–d

| Cancer | Compound VIa | | Compound VIb | | Compound VIc | | Compound VId | |
|---|---|---|---|---|---|---|---|---|
| | GI 50 | LC 50 | GI 50 | LC 50 | GI 50 | LC 50 | GI 50 | LC 50 |
| Leukemia | | | | | | | | |
| HL-60(TB) | −5.49 | −4.00 | −6.66 | −4.00 | −8.00 | −4.00 | −5.38 | −4.00 |
| K-62 | −4.58 | −4.00 | −5.76 | −4.00 | −7.63 | −4.00 | −5.46 | −4.20 |

TABLE 2-continued

Log LC50 (concentration in mol/L causing 50% lethality) Values for Compounds VI a–d

| Cancer | Compound VIa | | Compound VIb | | Compound VIc | | Compound VId | |
|---|---|---|---|---|---|---|---|---|
| | GI 50 | LC 50 | GI 50 | LC 50 | GI 50 | LC 50 | GI 50 | LC 50 |
| MOLT-4 | −5.68 | −4.10 | −6.50 | −4.08 | −8.00 | −4.00 | −4.79 | −4.00 |
| RPMI-8226 | −6.08 | −4.33 | −6.73 | −4.00 | −7.81 | −4.60 | −5.59 | −4.54 |
| SR | −6.68 | −5.21 | — | — | −8.00 | −5.62 | −5.37 | −4.00 |
| Non-small-cell lung | | | | | | | | |
| A549/ATCC | −4.10 | −4.00 | −4.37 | −4.00 | −7.23 | −4.00 | −4.66 | −4.00 |
| EKVX | −4.00 | −4.00 | −4.47 | −4.00 | −6.36 | −4.00 | −4.33 | −4.00 |
| HOP-62 | −4.46 | −4.00 | −5.14 | −4.00 | −8.00 | −4.00 | −4.00 | −4.00 |
| HOP-92 | −4.68 | −4.00 | −6.81 | −4.00 | −8.00 | −4.00 | −5.46 | −4.00 |
| NCI-H226 | −4.80 | −4.00 | −4.34 | −4.00 | −8.00 | −4.00 | −5.30 | −4.00 |
| NCI-H23 | −4.76 | −4.00 | −4.89 | −4.00 | −8.00 | −5.59 | −5.18 | −4.00 |
| NCI-H322 | −4.51 | −4.00 | −4.57 | −4.00 | −7.59 | −4.00 | −4.65 | −4.00 |
| NCI-H460 | −4.95 | −4.00 | −5.37 | −4.00 | −8.00 | −4.00 | −5.49 | −4.00 |
| NCI-H522 | −4.94 | −4.00 | −6.40 | −4.00 | −8.00 | −4.00 | −5.47 | −4.00 |
| Colon | | | | | | | | |
| COLO 205 | −4.66 | −4.00 | −5.34 | −4.00 | −7.99 | −6.26 | −5.49 | −4.00 |
| HCC-2998 | — | — | −4.73 | −4.04 | −7.95 | −4.00 | −5.69 | −4.29 |
| HCT-116 | −4.47 | −4.00 | −4.92 | −4.00 | −6.42 | −4.00 | −4.00 | −4.00 |
| HCT-15 | −4.39 | −4.00 | −4.25 | −4.00 | −7.92 | −6.37 | −4.25 | −4.00 |
| HT-29 | −4.58 | −4.00 | −4.46 | −4.00 | −8.00 | −4.00 | −5.02 | −4.00 |
| KM-12 | −4.70 | −4.04 | −4.64 | −4.00 | −7.84 | −4.67 | −5.25 | −4.00 |
| SW-620 | −4.68 | −4.00 | −6.23 | −4.00 | — | — | −5.49 | −4.00 |
| CNS | | | | | | | | |
| SF-268 | −4.95 | −4.00 | −5.52 | 4.00 | −8.00 | −4.00 | −5.44 | −4.00 |
| SF-295 | −5.06 | −4.00 | −4.99 | −4.00 | −8.00 | −4.69 | −5.30 | −4.00 |
| SF-539 | −4.97 | −4.00 | −6.21 | −4.00 | −8.00 | −4.00 | −5.44 | −4.00 |
| SNB-19 | −4.75 | −4.00 | −5.06 | −4.00 | −8.00 | −4.44 | −4.00 | −4.00 |
| SNB-75 | −4.23 | −4.00 | −4.61 | −4.00 | −7.94 | −4.00 | −4.51 | −4.00 |
| U251 | −4.87 | −4.00 | −5.41 | −4.00 | −8.00 | −4.41 | −5.47 | −4.00 |
| Melanoma | | | | | | | | |
| MALME-3M | −5.46 | −4.17 | −5.39 | 4.00 | −8.00 | −7.41 | — | — |
| LOXIMVI | — | — | — | — | — | — | −5.61 | −4.00 |
| M14 | −4.61 | 4.00 | −5.55 | −4.00 | −7.60 | −4.17 | −4.76 | −4.00 |
| SK-MEL-2 | −4.57 | −4.00 | −4.82 | −4.00 | −7.34 | −4.00 | — | — |
| SK-MEL-28 | −4.22 | −4.00 | −4.48 | −4.00 | −7.69 | −4.00 | −4.71 | −4.00 |
| SK-MEL-5 | −4.75 | −4.00 | −5.66 | −4.50 | −7.86 | −6.68 | −5.48 | −4.00 |
| UACC-257 | −4.49 | −4.00 | −4.45 | −4.00 | −7.65 | — | −4.75 | −4.00 |
| UACC-62 | −4.83 | −4.00 | −4.68 | −4.00 | −8.00 | −7.35 | −5.64 | −4.00 |
| Ovarian | | | | | | | | |
| IGROVI | −4.21 | −4.00 | −5.26 | −4.00 | −6.79 | −4.00 | −5.13 | −4.00 |
| OVCAR-3 | −4.68 | −4.00 | −5.47 | −4.00 | −7.91 | −4.00 | −5.32 | −4.00 |
| OVCAR-4 | −4.00 | −4.00 | −4.13 | −4.00 | −7.11 | −4.00 | −5.38 | −4.00 |
| OVCAR-5 | −4.65 | −4.00 | −5.06 | −4.00 | −7.92 | −4.00 | −5.33 | −4.00 |
| OVCAR-8 | −4.58 | −4.00 | −4.48 | −4.00 | −8.00 | −4.00 | −4.67 | −4.00 |
| SK-OV-3 | −4.00 | −4.00 | — | — | — | −4.00 | — | — |
| Renal | | | | | | | | |
| 786-0 | −4.84 | −4.00 | −5.30 | −4.00 | −8.00 | −4.00 | −5.61 | −4.00 |
| A498 | −4.29 | −4.00 | −5.73 | −4.00 | −6.89 | — | −5.00 | −4.00 |
| ACHN | −4.82 | −4.00 | −4.47 | −4.00 | −8.00 | −4.00 | −4.63 | −4.00 |
| CAKI-1 | −5.04 | −4.00 | −4.65 | −4.00 | −8.00 | −4.28 | −5.77 | −4.00 |
| RXF 393 | −4.23 | −4.00 | −5.68 | −4.09 | −7.54 | −4.00 | −8.00 | −5.09 |
| SN12C | −4.90 | −4.00 | −4.44 | −4.00 | −8.00 | −4.00 | −5.66 | −4.00 |
| TK-10 | −4.63 | −4.00 | −5.10 | −4.00 | −7.69 | −4.00 | — | −4.00 |
| UO-31 | −4.12 | −4.00 | −4.27 | −4.00 | −6.65 | −4.00 | −4.00 | −4.00 |
| Prostate | | | | | | | | |
| PC-3 | −4.44 | −4.00 | −5.53 | −4.00 | −7.02 | −4.00 | −5.41 | −4.00 |
| DU-145 | −4.36 | −4.00 | −5.62 | −4.00 | −7.60 | −4.00 | −5.37 | −4.00 |
| Breast | | | | | | | | |
| MCF7 | −4.88 | −4.00 | −6.01 | −4.00 | −8.00 | −4.00 | −5.69 | −4.00 |
| NCI/ADR-RES | −4.00 | −4.00 | −4.00 | −4.00 | −6.47 | −4.00 | −4.00 | −4.00 |
| MDA-MB-231/ATCC | −4.67 | −4.00 | −4.52 | −4.00 | −7.47 | −4.43 | −5.42 | −4.00 |
| HS578T | −4.34 | −4.00 | −6.13 | −4.00 | −7.30 | −4.00 | −5.12 | −4.00 |
| MDA-MB-435 | −4.71 | −4.08 | −5.37 | −4.09 | −7.87 | −7.15 | −5.37 | −4.00 |

TABLE 2-continued

Log LC50 (concentration in mol/L causing 50% lethality) Values for Compounds VI a–d

| Cancer | Compound VIa | | Compound VIb | | Compound VIc | | Compound VId | |
|---|---|---|---|---|---|---|---|---|
| | GI 50 | LC 50 | GI 50 | LC 50 | GI 50 | LC 50 | GI 50 | LC 50 |
| BT-549 | −4.56 | −4.00 | −5.77 | −4.00 | −7.68 | −4.00 | −5.31 | −4.00 |
| T-47D | −4.57 | −4.00 | −5.16 | −4.00 | −8.00 | −4.00 | −5.00 | −4.00 |

What is claimed is:

1. A compound of the formula (VI)

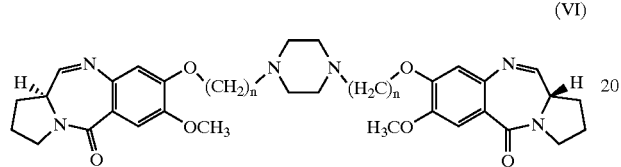

(VI)

where n=2 to 10.

2. A process for preparing a compound according to claim 1, the process comprising steps of:
 a) reacting (2S)-N-(4-hydroxy-5-methoxy-2-nitrobenzoyl) pyrrolidine-2-carbox-aldehyde diethylthioacetal) with a 1,n-dibromoalkane, where n=2 to 10, in water miscible organic solvent in presence of a base at a reflux temperature for a period of 20 h to 48 h,
 b) pouring the reaction mixture of step (a) onto water, extracting with ethylacetate, separating the ethylacetate layer and discarding the aqueous layer,
 c) evaporating the ethylacetate layer of step (b) to obtain a residue which is further purified to obtain the pure compound (2S)-N-[4-(2-bromoethoxy)-5-methoxy-2-nitrobenzolyl]pyrrolidine-2-carboxaldehyde diethyl thioacetal,
 d) providing a solution (2S)-N-[4-(2-bromoethoxy)-5-methoxy-2-nitrobenzolyl]pyrrolidine-2-carboxaldehyde diethyl thioacetal in a ketonic solvent in presence of a base at a reflux temperature for a period of 20 h to 48 h,
 e) pouring the reaction mixture of step (d) onto water, extracting with ethylacetate, separating ethylacetate layer, evaporating ethylacetate layer to obtain a residue, purifying the residue to get compound 1,1'-{[(bisethane-1,N-diyl)piperazine]dioxy}bis[(11aS)-7-methoxy-2-nitro-benzoylpyrrolidin-2-carboxaldehyde diethylthioacetal],
 dissolving the compound1,1'-{[(bisethane-1,N-diyl)piperazine]dioxy}bis](11aS)-7-methoxy-2-nitro-benzoylpyrrolidin-2-carboxaldehyde diethylthioacetal]in alcohol, adding stannous chloride dihydrate, refluxing for 0.5 h to 1.5 h, adjusting the pH of the reaction mixture of step (f) to 8.0 using alkali bicarbonate solution,
 extracting solution of pH 8.0 of step (g) with ethylacetate, separating the ethylacetate extract, drying the ethylacetate extract over anhydrous sodium sulphate, filtered and evaporated ethyl acetate solution to yield a crude compound 1,1'-{]bisethane-1,N-diyl)piperazine]dioxy}bis(11aS)-7-methoxy 2-aminobenzoylpyroolidin-2-carboxaldehyde diethylthioacetal],
 dissolving the compound 1,1'-{[bisethane-1,N-diyl)piperazine]dioxy}bis(11aS)-7-methoxy 2-aminobenzoylpyroolidin-2-carboxaldehyde diethylthioacetal] of step (h) in a mixture of acetonitrile/water, adding mercuric chloride, mercuric oxide and stirring for 6 h to 12 h at an ambient temperature,
 evaporating the organic layer of step (i), diluting the residue with ethylacetate, adding saturated bicarbonate solution at room temperature, filtering through a celite bed, washing with ethyl acetate to obtain a clear filterate; and
 evaporating the filtrate of step (j) to obtain a residue which is purified over silica gel column to yield a pure compound of formula (VI).

3. The process of claim 2, wherein in step (a) the base used is selected from the group consisting of lithium carbonate, sodium carbonate, potassium carbonate or cesium carbonate.

4. The process of claim 2, wherein in step (d) the ketonic solvent used is selected from the group consisting of acetone, methyl ethyl ketone and methyl isobutylketone.

5. The process of claim 2, wherein in step (d) the base used is selected from the group consisting of lithium carbonate, sodium carbonate, potassium carbonate and cesium carbonate.

6. The process of claim 2, wherein in step (f) the alcohol used, is selected from the group consisting of methanol, ethanol and isopropanol.

7. The process of claim 6, wherein the alcohol used is methanol.

8. A pharmaceutical composition comprising an effective amount of a compound of formula (VI) according to claim 1 and a pharmaceutically acceptable carrier.

9. A method for treating a tumor of a type selected from the group consisting of leukemia, non-small cell lung cancer, colon cancer, a central nervous system tumor, melanoma, ovarian cancer, renal cancer, prostate cancer, and breast cancer, comprising administering to a subject exhibiting a tumor an amount of the pharmaceutical composition of claim 8 effective to treat said tumor.

* * * * *